(12) United States Patent
Lignell et al.

(10) Patent No.: US 6,475,547 B1
(45) Date of Patent: *Nov. 5, 2002

(54) IMMUNOGLOBULIN-RICH MILK, PRODUCTION AND USE THEREOF

(75) Inventors: Ake Lignell; Johan Inborr, both of Varmdo (SE)

(73) Assignee: AstaCarotene AB, Gustavsberg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/581,189
(22) PCT Filed: Dec. 2, 1998
(86) PCT No.: PCT/SE98/02069
§ 371 (c)(1),
(2), (4) Date: Jul. 25, 2000
(87) PCT Pub. No.: WO99/30700
PCT Pub. Date: Jun. 24, 1999

(30) Foreign Application Priority Data

Dec. 18, 1997 (SE) .............................................. 9704737

(51) Int. Cl.[7] .............................................. A23C 23/00
(52) U.S. Cl. ........................ 426/580; 426/2; 426/540; 426/541; 514/725
(58) Field of Search ........................... 426/2, 580, 583, 426/540, 541; 514/725

(56) References Cited

U.S. PATENT DOCUMENTS 6,054,491 A * 4/2000 Lignell et al. ............... 514/725

FOREIGN PATENT DOCUMENTS

| EP | 0085005 A | 8/1983 |
| EP | 0173999 A | 3/1986 |
| SE | 9300901 A | 9/1994 |
| WO | 9735491 A | 10/1997 |
| WO | 97/35491 | * 10/1997 |
| WO | 9743905 A | 11/1997 |

OTHER PUBLICATIONS

File WPI, Derwent accession No. 88–195814, Taiyo Chem Ind Co Ltd: "Cosmetic material for curing acne—includes milk immunoglobulin as effective agent, used as cream, lotion etc.".

File WPI, Derwent accession No. 81–16842D, Influenza Res Inst: "Treatment of acute respiratory viral infections—includes administration via nasal cavities of secretory immunoglobulin from female colostrum".

* cited by examiner

Primary Examiner—Leslie Wong
(74) Attorney, Agent, or Firm—Bacon & Thomas

(57) ABSTRACT

A method of producing immunoglobulin-rich milk, including colostrum, in mammalian mothers, is described. The method includes administration of an effective daily dosage of a preparation containing at least one type of xanthophylls, such as astaxanthin, to said mothers, e.g. cows. Immunoglobulin-rich milk, including colostrum, produced according to the method and immunoglobulin concentrates derived from such milk, including colostrum, are also disclosed. These products may be used as nutrient for mammals, and as raw material for diagnostics, human and veterinary medicines, dermatologic preparations and cosmetics industry.

12 Claims, No Drawings

IMMUNOGLOBULIN-RICH MILK, PRODUCTION AND USE THEREOF

This application is a National stage filing of PCT /SE98/02069, filed Dec. 2, 1998.

The present invention relates to a method of producing immunoglobulin-rich milk, including colostrum, in mammalian mothers. The method comprises administration of at least one type of xanthophylls, such as astaxanthin, to said mothers, starting a few weeks prior to parturition and continuing during the lactation period. The invention also relates to the milk produced by the method, and the use of the milk as nutrition for mammals or as raw material for diagnostics, human and veterinarian medicines, dermatologic preparations and cosmetics industry.

BACKGROUND

Immunoglobulins are used in diagnostics, human and veterinary medicines, dermatologic preparations and cosmetics industry.

Ingestion of mother's milk is of crucial importance for the growth and health status of the new-born mammal. The milk is the primary source of energy, proteins, fat and other essential nutrients during the breast feeding/suckling period. In case, for one reason or another, the offspring cannot get its one mother's milk, milk from another mother or from milk powder products are fed.

After birth the new-born mammal starts building up its immune defense by suckling and drinking colostrum from its mother. In addition to providing energy and nutrients for growth, colostrum contains a high concentration of so-called immunoglobulins (large protein molecules), which are readily absorbed into the blood of the newborn. These immunoglobulins are the fundamental substances for building up the immune defense system. The more immunoglobulins in the colostrum the greater the probability of obtaining a well working defense against infections and diseases.

In some mammalian species, the ability to take up the large immunoglobulin molecules is restricted to the first few hours after birth. After the so called "gut closure" has occurred the absorption of immunoglobulins is limited. Consequently, a high concentration of immunoglobulins in colostrum immediately after birth appears to be of utmost importance for maintaining a good health status of the newborns.

Our published International patent application WO 97/35491 relates to an agent for increasing the production of/in breeding and production mammals, and discloses experiments wherein sows were given feed supplemented with astaxanthin during a period prior to parturition and during lactation resulting in e.g. more piglets born alive.

Astaxanthin, and other xanthophylls, are known to exhibit antioxidative properties, and hence possess the ability to scavenge so-called free radicals. However, in biological tests astaxanthin has been shown to possess clearly the best antioxidative properties compared to other carotenoids (Miki W., 1991, Pure and Appl Chem 63 (1): 141–146).

DESCRIPTION OF THE INVENTION

The present invention is directed to a method of producing immunoglobulin-rich milk, including colostrum, in mammalian mothers, comprising administration of an effective daily dosage of a preparation containing at least one type of xanthophylls to said mothers, starting a few weeks prior to parturition and continuing during the lactation period.

The mammal may be human or non-human, especially cow, sow, and goat. In a preferred embodiment the mammal is a cow.

In another preferred embodiment the type of xanthophylls is astaxanthin. In a particularly preferred embodiment the astaxanthin exists in a form in which it is esterified with fatty acids. The last mentioned form of astaxanthin may be in the form of algal meal produced by culturing of the alga Haematococcus sp.

An effective dosage of the preparation contains e.g. 0.01 to 1 mg astaxanthin per kg body weight per day.

In the present invention the preparation may comprise a mixture of different types of xanthophylls or different forms of the same xanthophyll, such as a mixture of synthetic astaxanthin and naturally produced astaxanthin.

The xanthophyll-preparation of the invention may comprise additional ingredients which are biologically inactive or active, such as flavoring agents, excipients, diluents, carriers, etc., and it may be presented in a separate unit dose or in admixture with food or feed. Examples of separate unit doses are tablets, gelatin capsules and predetermined amounts of solutions, e. g. oil solutions, or emulsions, e.g. water-in- oil or oil-in-water emulsions. Examples of food in which the preparation of the invention may be incorporated is dairy products, such as yogurt, chocolate and cereals. Farm animals will normally receive the xanthophyll-preparation as a top dressing or mixed in their ordinary feed.

The present invention is also directed to the immunoglobulin-rich milk, including colostrum, which has been produced according to the method of the invention.

The immunoglobulin-rich milk, including colostrum, may be used as such, or may be used for the production of an immunoglobulin concentrate by e.g. ultrafiltration and lyophilization.

Thus, the invention is directed to an immunoglobulin concentrate derived from the immunoglobulin-rich milk, including colostrum, according to the invention.

Finally, the invention is directed to the use of the immunoglobulin-rich milk, including colostrum, according to the invention or the immunoglobulin concentrate according to the invention, as nutrient for mammals, and as raw material for diagnostics, human and veterinary medicines, dermatologic preparations and cosmetics industry.

Description of experiments

The xanthophyll-preparation used in the experiments contained astaxanthin which was produced via the alga Haematococcus sp. by AstaCarotene AB, Gustavsberg, Sweden.

Naturally produced astaxanthin can be obtained also from fungi and crustaceans, in addition to from alga. Astaxanthin from other sources, and other xanthophylls as well, are expected to be similarly useful for the purposes of the invention. An advantage of using astaxanthin from alga is, however, that the astaxanthin exists in a form esterified with fatty acids [Renström B. et al, 1981, Phytochem 20(11) :2561–2564], which esterified astaxanthin thereby is more stable during handling and storage than free astaxanthin.

Experimental Design and Results

Dairy cows were given algal meal (from *Haematococcus pluvialis*) to provide 100 mg natural astaxanthin per day during a period starting four weeks before calving and continuing during the first three months of lactation.

Colostrum was collected from three second lactation cows on the day after calving for analysis of immunoglobulins and compared to colostrum of cows of the same age on the same farm that had not been fed the algal meal. Surprisingly, the concentration of immunoglobulins in colostrum of cows fed the algal meal was 43 per cent higher than in colostrum of the control cows. It appears that the algal meal rich in astaxanthin increases the concentration of immunoglobulins in milk, especially colostrum.

We claim:

1. An immunoglobulin concentrate derived from milk with an increased concentration of immunoglobulins produced in mammalian mothers by administration of an effective daily dosage of a preparation containing astaxanthin to said mothers, starting a few weeks prior to parturition and continuing during the lactation period.

2. The immunoglobulin concentrate of claim 1, wherein the mammalian mother is a cow.

3. The immunoglobulin concentrate of claim 1, wherein the astaxanthin exists in a form esterified with fatty acids.

4. The immunoglobulin concentrate of claim 3, wherein the esterified astaxanthin is in the form of algal meal produced by culturing of the alga Haematococcus sp.

5. The immunoglobulin concentrate of claim 3, wherein the effective dosage of the preparation contains 0.01 to 1 mg astaxanthin per kg body weight per day.

6. The immunoglobulin concentrate of claim 4, wherein the effective dosage of the preparation contains 0.01 to 1 mg astaxanthin per kg body weight per day.

7. An immunoglobulin concentrate derived from colostrum containing an increased concentration of immunoglobulins produced in mammalian mothers by administration of an effective daily dosage of a preparation containing astaxanthin to said mothers, starting a few weeks prior to parturition and continuing during the lactation period.

8. The immunoglobulin concentrate of claim 7, wherein the mammalian mother is a cow.

9. The immunoglobulin concentrate of claim 7, wherein the astaxanthin exists in a form esterified with fatty acids.

10. The immunoglobulin concentrate of claim 9, wherein the esterified astaxanthin is in the form of algal meal produced by culturing of the alga Haematococcus sp.

11. The immunoglobulin concentrate of claim 9, wherein the effective dosage of the preparation contains 0.01 to 1 mg astaxanthin per kg body weight per day.

12. The immunoglobulin concentrate of claim 10, wherein the effective dosage of the preparation contains 0.01 to 1 mg astaxanthin per kg body weight per day.

* * * * *